United States Patent [19]

Thornton

[11] Patent Number: 5,109,871
[45] Date of Patent: May 5, 1992

[54] HEALTH PRODUCT

[76] Inventor: Thomas F. Thornton, 43 Contentment Island Rd., Darien, Conn. 06820

[21] Appl. No.: 678,142

[22] Filed: Apr. 1, 1991

[51] Int. Cl.⁵ ............................................. A61F 6/00
[52] U.S. Cl. .................................... 128/844; 128/842
[58] Field of Search ............... 128/842, 844, 917, 918; D24/105

[56]  References Cited

U.S. PATENT DOCUMENTS

| D. 252,949 | 9/1979 | Okamoto | 128/844 X |
| 2,586,674 | 2/1952 | Lonne | 128/844 |
| 4,881,553 | 11/1989 | Grossman | 128/844 |
| 4,919,149 | 4/1990 | Stang | 128/842 |

Primary Examiner—Robert A. Hafer
Assistant Examiner—Sam Rimell
Attorney, Agent, or Firm—Dallett Hoopes

[57] ABSTRACT

Prophylactic device has a ribbed exterior surface, the ribs being generally parallel and commencing adjacent the distal or closed end of the device, each at an angle of about 10° to the longitudinal and arcing away from the longitudinal to terminate adjacent the proximate or open end at an angle of about 44° to the longitudinal. The purpose of the ribs is to heighten stimulation of the woman.

6 Claims, 1 Drawing Sheet

HEALTH PRODUCT

BACKGROUND OF THE INVENTION

1. Field of the Invention

The present invention relates to prophylactic devices of the type normally employed to prevent the transmission of venereal diseases and for purposes of birth control. The present invention achieves these purposes and also provides supplementary stimulation of the woman during copulation.

2. Description of Related Art including Information Disclosed under §§1.97 to 1.99

The prior art includes disclosures of various prophylactic devices, or condoms, in which the external surface is formed with ribs or other projections for the purpose of stimulating the woman during copulation. An example is the disclosure in U.S. Pat. No. 3,809,090 which issued May 7, 1974 to Povlacs et al. The projections in this patent are in the form of interrupted rings which may be canted with respect to the radial plane. Helical patterns are also taught.

The design art also includes showings of designs which also include ribbed arrangements. Examples are U.S. Pat. No. 252,949 which issued on Sept. 18, 1979 and U.S. Pat. No. 253,009 which issued Sept. 25, 1979, both to Tadao Okamoto.

SUMMARY OF THE INVENTION

For ease of understanding, references to the condom herein will be expressed as though the condom were in its generally cylindrical condition as presented in the drawings.

The present invention is a condom having a plurality of generally parallel longitudinal ribs spaced about its outside surface. The ribs each commence adjacent the distal end or closed end of the condom at an angle in the range of 5° to 15° to an imaginary longitudinal line along the surface of the condom and arcs to terminate an angle in the range of 35° to 44° to another imaginary longitudinal line along the surface of the condom adjacent the proximate or open end of the condom. Thus reciprocal movement of the condom along its axis produces a lateral component of movement in the rib with respect to a fixed contiguous point thereadjacent.

The velocity of the lateral component of movement of a rib vis-a-vis any fixed narrow circumferential band of contiguous tissue surrounding the outside of the condom will depend on the angle away from the longitudinal of the rib at a given instant and, of course, the velocity and direction of axial movement of the condom. Thus, as the angle increases from the distal end of the condom at 5° to the proximate end at 44°, the velocity of the lateral component of movement will increase. Specifically, taking the same hypothetical fixed narrow circumferential band of tissue contiguous to the body, the lateral component of movement of a rib will, during the inward movement of the condom, commence at slow lateral speed and accelerate in one direction and then in the outward movement of the condom, commence at high lateral speed in the reverse direction and decelerate. The higher velocities will be when the condom is moving proximate its inward most position.

Thus, the present invention enhances pleasurable sensation during copulation by effecting for a woman a perceived lateral movement of parts which movement accelerates and decelerates during the stroking cycle.

BRIEF DESCRIPTION OF THE DRAWINGS

Other features and objects of the invention will be apparent to those skilled in the art from the following specification and the drawings, all of which disclose a preferred embodiment of the invention. In the drawings.

DESCRIPTION OF THE PREFERRED EMBODIMENT

Figure 1:
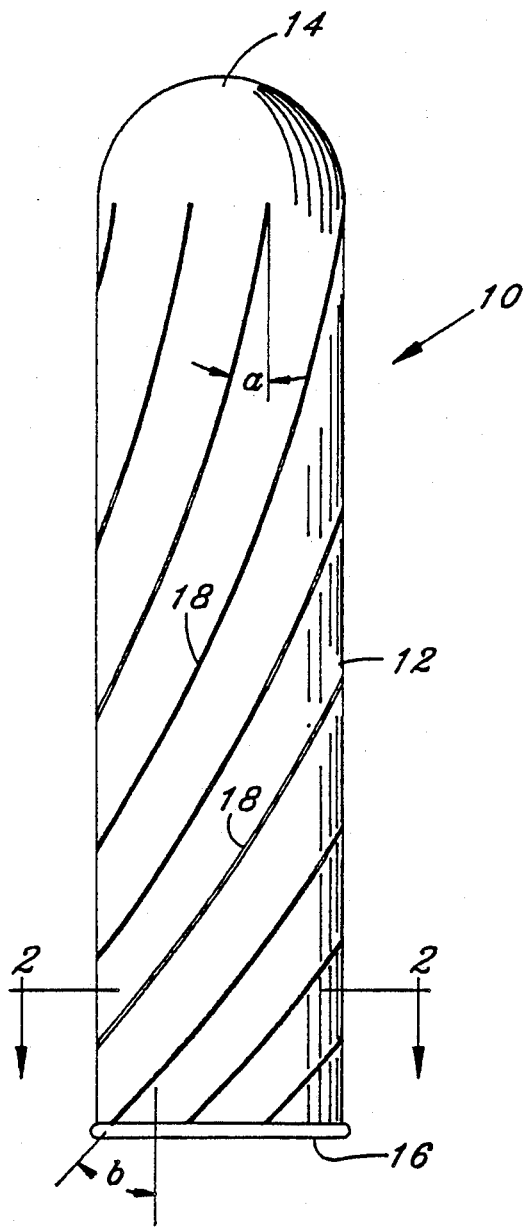
FIG. 1 is an elevational view of a prophylactic device having peripherally extending ribs in accordance with the present invention.

A condom embodying the invention is shown in FIG. 1 and generally designated 10. It comprises the usual latex skin which may have a thickness of 0.002 inches and includes a cylindrical section 12 a domed section 14 and the rolled annular section 16. Herein the end having the dome is the closed or distal end and the end having the rolled annular section 16 is the open or proximate end.

Figure 2:
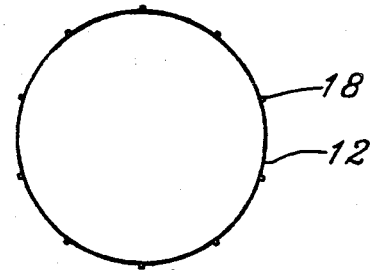
FIG. 2 is a sectional view taken on the line 2—2 of FIG. 1.

Formed on the exterior of the condom are the ribs 18. The ribs are generally parallel and uniformly spaced about the circumference of the article (FIG. 2). The ribs are in a range of 0.005 inches to 0.050 inches high from the adjacent surface of the condom and in a range of 0.005 inches to 0.050 inches thick.

An essential element of the invention is the shape of the ribs and their disposition on the condom. As shown in FIG. 1, the ribs commence adjacent the closed or distal end of the condom at an angle a to an imaginary line disposed longitudinally of the condom. In practice angle a is in the range of 0° to 20°, 10° being preferred. In development, the ribs then swing in a true arc down toward the open or proximate end of the condom. In other words, if the surface of the condom were laid out in a flat sheet, the ribs would be shown to be arcs having their respective centers spaced along a straight line. In an actual embodiment in the form of a flat sheet, the ribs are arcs having 9" radii.

The ribs extend down toward the closed or proximate end, their angle measured against the longitudinal increasing as the proximate end is approached. At their ends the ribs intersect a second imaginary longitudinal line at an angle b which is in the range of 35° to 44°. Instead of simple arcs, irregular arcs of accelerated curvature are contemplated in order to accentuate the velocity effect toward the proximate end.

Figure 3:
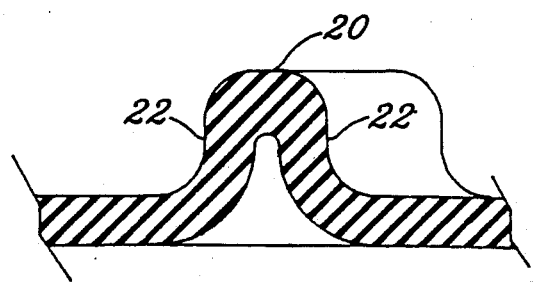
FIG. 3 is a greatly enlarged sectional view taken in a radial plane across a rib of FIG. 1.

As shown in section in FIG. 3, the ribs are generally rounded on their top surface at 20. The side walls 22 of the ribs are generally perpendicular to the surface of the condom, except that a filet blends each sidewall into the surface of the condom as shown.

In general, it has been found that steep angles of the ribs with respect to the radial result in the best performance of the articles under the invention. The more nearly longitudinal the rib, of course, the stronger the lateral force, but at the same time, the less the kinetic effect. On the other hand, when the angle with the longitudinal approaches 45°, to say 44°, the lateral force is less strong, but the kinetic effect is greater. Over 45°, that is, a flatter angle, the lateral force component weakens, but the speed of lateral movement increases. This increase in speed of lateral movement may actually cause discomfort if the height of the ribs is too great. Reduced height of the ribs where the pitch is flat may be called for to avoid excessive working of the tissues. Hence, with ribs of uniform height, angles to the longitudinal of no more than 44° are preferred (See FIG. 1). Indeed, instead of being developed from arcs, as described above, some benefit of the invention can be enjoyed by forming the ribs in a constant angle in the range of 10° to 44° to the longitudinal. The ribs with the changing angle as shown in FIG. 1 are preferred.

The integral structure of the condom wall and the ribs are simultaneously provided in the molding process. The condom is formed by the dipping of a preformed stainless steel, aluminum, plastic or glass mandrel into a latex solution. The latex solution tends to adhere to the mandrel upon thereof to provide a solution, and it flows along the surface thereof to provide a uniform latex coating which ultimately forms the condom wall.

In order to provide the integral ribs 18, the desired rib pattern is initially cut into the mandrel corresponding to the ribs which are to be formed The immersion of the mandrel into the latex solution results in the formation of a condom having a wall including the peripherally extending ribs. The inside or interior surface of the condom is smooth as a result of the flow properties of the latex solution which evenly distribute the latex on the mandrel during the dipping process. Prior to use the condom is turned inside out so that the ribs, which are initially molded on the interior surface, are on the outside.

It is, of course, possible to provide ribs of increased thickness or height by increasing the depth of the recesses cut into the mandrel.

While the invention has been shown in only one embodiment, it is not so limited but is of a scope defined the the following claim language and may be broadened by a extension of the right to exclude others from making or using the invention as is appropriate under the doctrine of equivalents.

I claim:

1. A condom having a tubular wall and a plurality of generally parallel curving longitudinal ribs spaced about the surface thereof, the ribs being the same in direction and curvature, each commencing adjacent the distal end of the condom at a first angle in the range of 0° to 20° to an imaginary longitudinal line along the surface of the condom and curving away from said line and terminating adjacent the proximate end at a second angle in the range of 35° to 44° to another imaginary longitudinal line along the surface of the condom each rib being a unitary part of said tubular wall of said condom.

2. A condom having a plurality of curving longitudinal ribs spaced about the outside surface thereof, the ribs each commencing adjacent the distal end of the condom at a first angle in the range of 0° to 20° to an imaginary longitudinal line along the surface of the condom and terminating adjacent the proximate end at a second angle in the range of 35° to 44° to another imaginary longitudinal line along the surface of the condom, the ribs being in a pattern such that if the surface of the condom were cut longitudinally and laid out flat, the ribs would be uniform arcs swung from centers spaced along a straight line.

3. A condom as claimed in claim 1 wherein the ribs commence at the same distance from the extreme distal end of the body.

4. A condom as claimed in claim 1 wherein the ribs are uniformly spaced about the circumference of the condom.

5. A condom as claimed in claim 1 wherein the ribs are on the order of a range of 0.005 inches to 0.050 inches in height and 0.005 inches to 0.050 inches in width.

6. A condom as claimed in claim 1 wherein the first angle is approximately 10° and the second angle is approximately 44°.

* * * * *